(12) United States Patent
Ishima et al.

(10) Patent No.: US 9,969,702 B2
(45) Date of Patent: May 15, 2018

(54) TRIAZINE COMPOUND AND SYNTHETIC RESIN COMPOSITION USING SAME

(71) Applicant: ADEKA CORPORATION, Tokyo (JP)

(72) Inventors: Yosuke Ishima, Saitama (JP); Mio Tanabe, Saitama (JP); Masahiro Oishi, Saitama (JP); Takashi Mutou, Saitama (JP)

(73) Assignee: ADEKA CORPORATION, Tokyo (JP)

(*) Notice: Subject to any disclaimer, the term of this patent is extended or adjusted under 35 U.S.C. 154(b) by 0 days. days.

(21) Appl. No.: 15/522,029

(22) PCT Filed: Dec. 1, 2015

(86) PCT No.: PCT/JP2015/083724
§ 371 (c)(1),
(2) Date: Apr. 26, 2017

(87) PCT Pub. No.: WO2016/093108
PCT Pub. Date: Jun. 16, 2016

(65) Prior Publication Data
US 2017/0327475 A1 Nov. 16, 2017

(30) Foreign Application Priority Data

Dec. 11, 2014 (JP) ................................. 2014-250555
Nov. 30, 2015 (JP) ................................. 2015-232704

(51) Int. Cl.
C07D 251/24 (2006.01)
C08K 5/3492 (2006.01)
(Continued)

(52) U.S. Cl.
CPC .......... C07D 251/24 (2013.01); C08K 5/3492 (2013.01); C08L 69/00 (2013.01); C09K 3/00 (2013.01)

(58) Field of Classification Search
CPC ....... C07D 251/24; C08L 69/00; C08L 67/00; C08K 5/3492; C09K 3/00
(Continued)

(56) References Cited

U.S. PATENT DOCUMENTS 3,249,608 A 5/1966 Hans et al.
5,189,084 A 2/1993 Birbaum et al.
(Continued)

FOREIGN PATENT DOCUMENTS

JP 43-21860 9/1968
JP 08-225679 9/1996
(Continued)

OTHER PUBLICATIONS

International Search Report, PCT/JP2015/083724, dated Mar. 8, 2016.

Primary Examiner — Venkataraman Balasubramanian
(74) Attorney, Agent, or Firm — Young & Thompson

(57) ABSTRACT

A novel compound excellent in heat resistance, resistance to volatilization, and compatibility with a resin component and useful as a UV absorber and a synthetic resin composition containing the compound are provided. Specifically provided are a triazine compound of general formula (1), preferably general formula (2) and a synthetic resin composition containing 0.001 to 20 parts by mass of the compound per 100 parts by mass of a synthetic resin. The details of formulae (1) and (2) are as defined in the description.

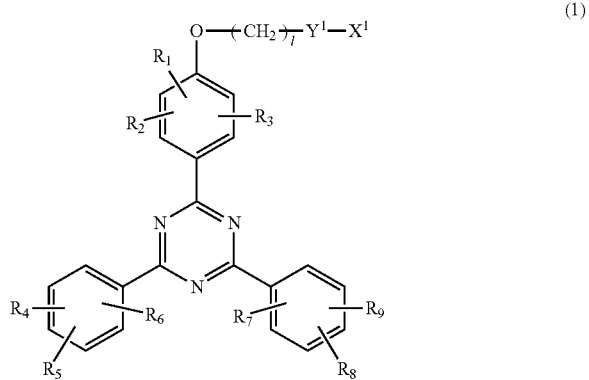

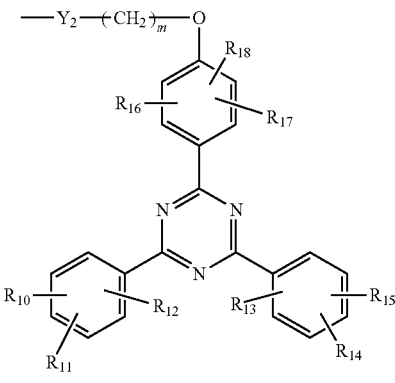

(Continued)

-continued

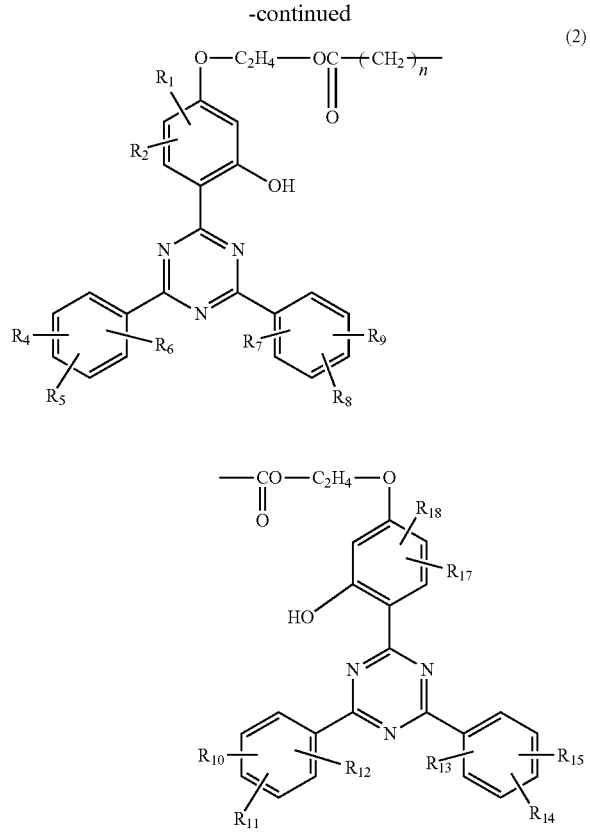

(51) Int. Cl.
C08L 69/00 (2006.01)
C09K 3/00 (2006.01)

(58) Field of Classification Search
USPC ......... 544/180, 216; 524/100; 428/412, 480; 252/405, 588, 509
See application file for complete search history.

(56) References Cited

U.S. PATENT DOCUMENTS

| | | | |
|---|---|---|---|
| 5,597,854 A | 1/1997 | Birbaum et al. | |
| 5,736,597 A | 4/1998 | Birbaum et al. | |
| 7,125,920 B2* | 10/2006 | Negishi | C07D 251/24 252/403 |
| 7,166,653 B2* | 1/2007 | Leppard | C07D 251/24 523/122 |
| 2002/0083641 A1 | 7/2002 | Leppard et al. | |
| 2003/0236327 A1 | 12/2003 | Leppard et al. | |
| 2004/0099849 A1 | 5/2004 | Negishi et al. | |
| 2005/0059758 A1 | 3/2005 | Leppard et al. | |

FOREIGN PATENT DOCUMENTS

| | | |
|---|---|---|
| JP | 10-17337 | 1/1998 |
| JP | 10-17556 | 1/1998 |
| JP | 10-17557 | 1/1998 |
| JP | 2002-114879 | 4/2002 |
| JP | 2003-192830 | 7/2003 |
| WO | WO 02/081559 | 10/2002 |

11 Claims, No Drawings

* cited by examiner

TRIAZINE COMPOUND AND SYNTHETIC RESIN COMPOSITION USING SAME

TECHNICAL FIELD

This invention relates to a novel compound excellent in heat resistance, resistance to volatilization, and compatibility with a resin component and useful as an ultraviolet (UV) absorber. The invention also relates to a synthetic resin composition containing the compound and a molded article of the composition.

BACKGROUND ART

Synthetic resins are widely used in a variety of fields in the form of molded articles, films, coatings, and so on. It is known, however, that molded articles made solely of synthetic resins deteriorate under natural light, particularly UV rays to undergo color change or reduction in mechanical strength and are therefore incapable of withstanding long periods of use. Therefore, resins for molded articles have been used in combination with a UV absorber and/or a light stabilizer so as to be protected from light deterioration. A triazine compound is known to have excellent UV absorbing effect as reported, e.g., in patent documents 1 to 6.

However, the effect of adding the triazine compounds of these patent documents has turned out to inadequate due to their insufficient resistance to heat or volatilization and insufficient compatibility with resin components.

CITATION LIST

Patent Document

Patent document 1: JP 43-021860B
Patent document 2: U.S. Pat. No. 5,189,084
Patent document 3: U.S. Pat. No. 5,736,597
Patent document 4: JP 10-017556A
Patent document 5: US 2004/099849
Patent document 6: JP 2003-192830A Taking, for instance, polycarbonate resins, they are excellent in heat resistance, impact resistance, transparency, and the like and widely used as engineering plastics in various applications, such as optical parts, mechanical parts, electric/electronic parts, automotive parts, resin glass, and building materials. However, polycarbonate resins have insufficient weatherability and deteriorate easily when exposed to UV light to undergo reduction of molecular weight, yellowing, and the like. The poor weatherability is of particular concern for outdoor use.

Adding a UV absorber to polycarbonate resins has been practiced to improve the weatherability. Examples of known UV absorbers include benzophenones, benzotriazoles, and cyanoacrylates. Triazines are also included as proposed in patent documents 4 and 5.

The problem with the use of the conventional UV absorbers resides in their poor heat resistance. That is, the UV absorber is volatilized by the heat of resin processing (e.g., extrusion or injection molding) to exhibit only a reduced effect or contaminates the processing equipment. The conventional UV absorbers are gradually volatilized also during outdoor use, eventually failing to exert long-term weatherability.

In addition, the conventional UV absorbers have poor compatibility with polycarbonate resins, resulting in impairment of transparency.

SUMMARY OF THE INVENTION

Problem to be Solved by the Invention

An object of the invention is to provide a novel compound excellent in not only resistance to heat and volatilization but compatibility with resin components and useful as a UV absorber and a synthetic resin composition using the compound.

Another object of the invention is to provide a polycarbonate resin composition that has excellent heat resistance and therefore does not reduce in performance during processing nor contaminate processing equipment and exhibits transparency and high weatherability and a molded article obtained from the composition.

Means for Solving the Problem

The inventors have conducted extensive studies with a view to solving the aforementioned problems and, as a result, found a specific triazine compound having a dimer structure useful as a UV absorber for synthetic resins and thus completed the present invention.

The invention provides in a first aspect a triazine compound represented by general formula (1):

[Chem.1]

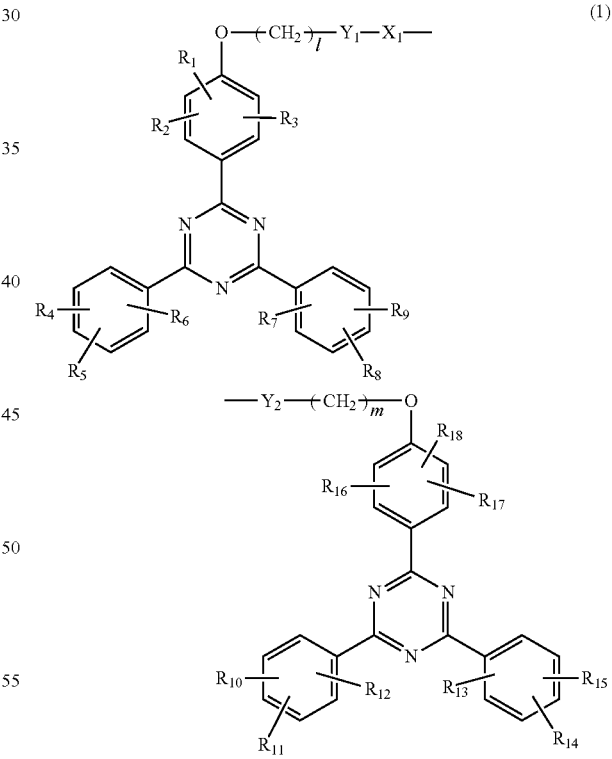

wherein $X^1$ represents an optionally branched and optionally substituted alkylene group having 8 or more carbon atoms; $Y^1$ and $Y^2$, which may be the same or different, each represent —COO—, —OCO—, -$L^1$-, —O-$L^1$O—, —O$L^1$-, -$L^1$OCO—, -$L^1$COO—, —CO—CH=CH—, —CH=CH—CO—, —CH=CH—COO—, —CH=CH—OCO—, or —COO—CH=CH—, wherein $L^1$ represents an optionally branched alkylene group having 1 to 8 carbon atoms; $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ any two or more of which may be the same or different, each represent a hydrogen atom, a hydroxy group, a halogen atom, an alkyl group having 1 to 20 carbon atoms, a alkenyl group having 3 to 20 carbon atoms, an alkoxy group having 1 to 20 carbon atoms, or an aryl group having 6 to 20 carbon atoms; and l and m, which may be the same or different, each represent an integer of 0 to 8.

The invention provides a preferred embodiment of the triazine compound which is represented by general formula (2):

[Chem.2]

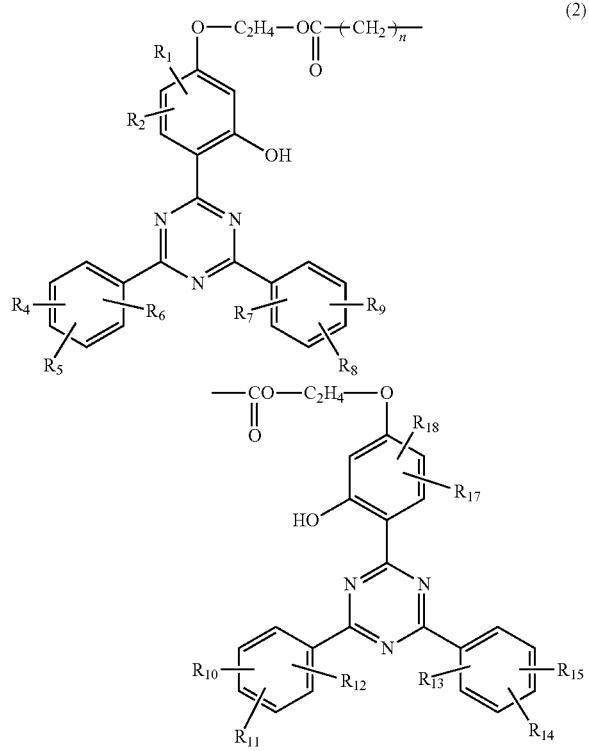

(2)

wherein $R^1$, $R^2$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{17}$, and $R^{18}$ are as defined for general formula (1); and n represents an integer of 8 to 14.

The invention provides another preferred embodiment of the triazine compound which is represented by general formula (3):

[Chem. 2A]

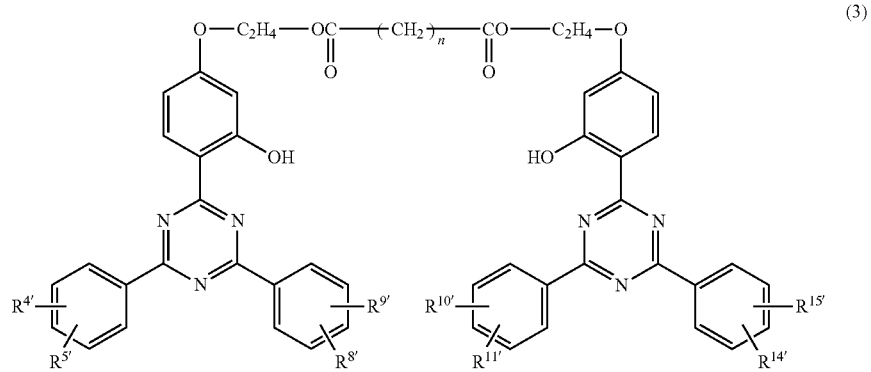

(3)

wherein $R^{4'}$, $R^{5'}$, $R^{8'}$, $R^{9'}$, $R^{10'}$, $R^{11'}$, $R^{14'}$, and $R^{15'}$, any two or more of which may be the same or different, each represent a hydrogen atom or an alkyl group having 1 to 4 carbon atoms; and n is as defined for general formula (2).

The invention provides in a second aspect a synthetic resin composition containing 100 parts by mass of a synthetic resin and 0.001 to 20 parts by mass of the triazine compound of the invention.

The invention provides a preferred embodiment of the synthetic resin composition in which the synthetic resin is a polycarbonate resin, a polyester resin, or an acrylic resin.

The invention also provides in a third aspect a molded article obtained from the synthetic resin composition of the invention.

In preferred embodiments where the synthetic resin is a polycarbonate resin, the invention provides a polycarbonate resin composition which contains 100 parts by mass of a polycarbonate resin and 0.001 to 20 parts by mass of the triazine compound of formula (1), preferably formula (2), more preferably formula (3), as a UV absorber; and a transparent molded article obtained from the polycarbonate resin composition.

Effect of the Invention

The invention provides a novel compound excellent in heat resistance, resistance to volatilization, and compatibility with a resin component and useful as a UV absorber and a synthetic resin composition using the compound.

The invention also provides a polycarbonate resin composition that has excellent heat resistance and therefore does not reduce in performance during processing nor contaminates processing equipment and exhibits excellent transparency and weatherability. The invention also provides a polycarbonate resin molded article excellent in transparency and weatherability.

EMBODIMENTS FOR CARRYING OUT THE INVENTION

The invention will be described in detail on the basis of its preferred embodiments.

The triazine compound of the invention is a novel compound represented by general formula (1) and characterized by having two triazine structures linked together via a specific group.

In formula (1), $X^1$ is an optionally branched and optionally substituted alkylene group having more than 7 carbon atoms. Examples of $X^1$ include straight-chain alkylene groups, such as $—(CH_2)_8—$, $—(CH_2)_9—$, $—(CH_2)_{10}—$, $—(CH_2)_{11}—$, $—(CH_2)_{12}—$, $—(CH_2)_{13}—$, and $—(CH_2)_{14}—$; and those listed above having one or more of their hydrogen atoms substituted by an alkyl group with 1 to 8 carbon atoms, a halogen atom, a hydroxy group, an alkoxy group, and so on. In the interests of compatibility with resins, heat resistance, and resistance to volatilization, $X^1$ is preferably a straight-chain alkylene group $—(CH_2)_n—$ ($8 \leq n \leq 14$, more preferably $10 \leq n \leq 12$), particularly preferably a straight-chain alkylene group $—(CH_2)_{10}—$. Compounds in which n is fewer than 8 are poor in compatibility with resins.

$Y^1$ and $Y^2$, which may be the same or different, each represent —COO—, —OCO—, -$L^1$-, —O-$L^1$O—, —O$L^1$—, -$L^1$OCO—, -$L^1$COO—, —CO—CH=CH—, —CH=CH—CO—, —CH=CH—COO—, —CH=CH—OCO—, or —COO—CH=CH—, wherein $L^1$ represents an optionally branched alkylene group having 1 to 8 carbon atoms.

$Y^1$ and $Y^2$ each preferably represent —COO— or —OCO— in terms of compatibility with resins, heat resistance, and resistance to volatilization.

$R^1$ through $R^{18}$, any two or more of which may be the same or different, each represent a hydrogen atom, a hydroxy group, a halogen atom, a C1-C20 alkyl group, a C3-C20 alkenyl group, C1-C20 alkoxy group, or a C6-C20 aryl group, and l and m, which may be the same or different, each represent an integer of 0 to 8.

Examples of the halogen atom as $R^1$ to $R^{18}$ are fluorine, chlorine, and bromine.

Examples of the C1-C20 alkyl group include methyl, ethyl, propyl, 2-propyl, butyl, isobutyl, s-butyl, t-butyl, pentyl, isopentyl, hexyl, decyl, dodecyl, and octadecyl.

Examples of the C3-C20 alkenyl group include vinyl, 1-propenyl, isopropenyl, 2-methyl-1-propenyl, 1-butenyl, 2-butenyl, 3-butenyl, 2-ethyl-1-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, and 5-hexenyl.

Examples of the C1-C20 alkoxy group include methoxy, ethoxy, isopropoxy, butoxy, s-butoxy, t-butoxy, isobutoxy, amyloxy, isoamyloxy, t-amyloxy, hexyloxy, 2-hexyloxy, 3-hexyloxy, cyclohexyloxy, 4-methylcyclohexyloxy, heptyloxy, 2-heptyloxy, 3-heptyloxy, isoheptyloxy, t-heptyloxy, 1-octyloxy, isooctyloxy, and t-octyloxy.

Examples of the C6-C20 aryl group include phenyl, naphthyl, anthracenyl, phenanthryl, fluorenyl, indenyl, 2-methylphenyl, 3-methylphenyl, 4-methylphenyl, 4-vinylphenyl, 3-isopropylphenyl, 4-isopropylphenyl, 4-butylphenyl, 4-isobutylphenyl, 4-t-butylphenyl, 4-hexylphenyl, 4-cylcohexylphenyl, 4-octylphenyl, 4-(2-ethylhexyl)phenyl, 4-stearylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4-di-t-butylphenyl, 2,5-di-t-butylphenyl, 2,6-di-t-butylphenyl, 2,4-di-t-pentylphenyl, 2,5-di-t-amylphenyl, 2,5-di-t-octylphenyl, 2,4-dicumylphenyl, 4-cyclohexylphenyl, (1,1'-biphenyl)-4-yl, 2,4,5-trimethylphenyl, and ferrocenyl. $R^1$ through $R^{15}$ are each preferably hydrogen, C1-C4 alkyl, or hydroxyl in terms of compatibility with resins, heat resistance, and resistance to volatilization.

Letters l and m, which may be the same or different, each represent an integer 0 to 8, preferably 2 to 4, more preferably 2.

Of the triazine compounds of formula (1) preferred are those represented by general formula (2) below, particularly those represented by general formula (3) below in terms of absorbance and ease of synthesis (with reduced by-product formation).

[Chem.2B]

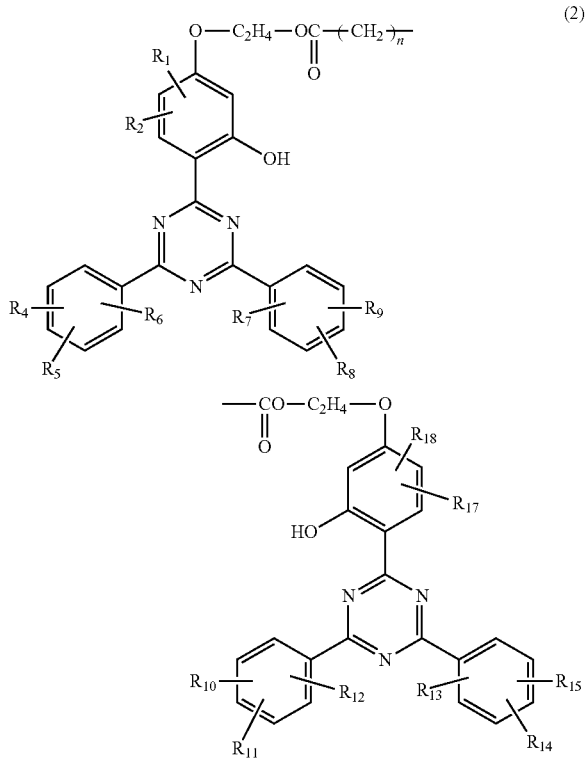

(2)

wherein $R^1$, $R^2$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{17}$, and $R^{18}$ are as defined for general formula (1); and n represents an integer of 8 to 14.

[Chem.2C]

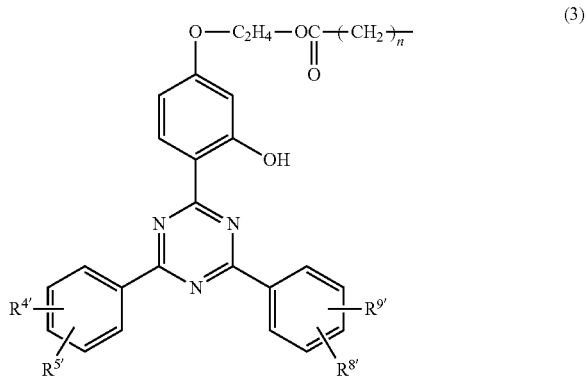

(3)

-continued

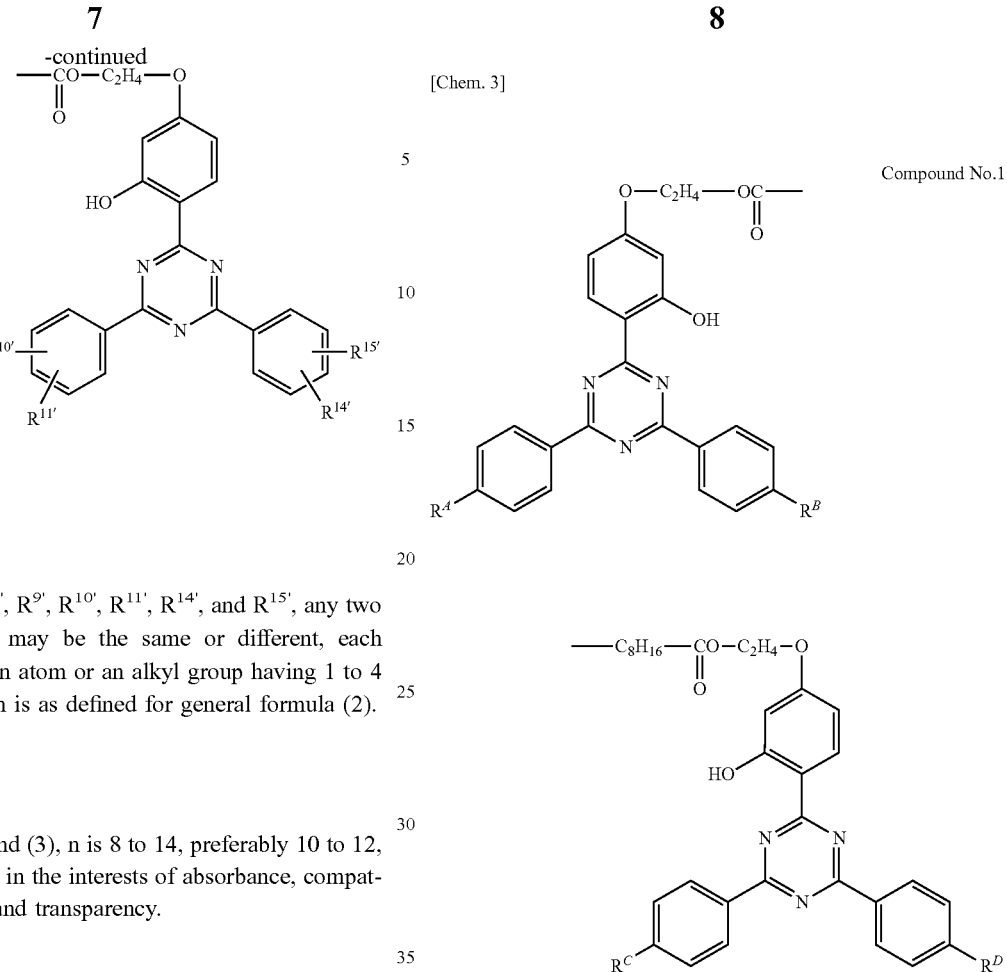

wherein $R^{4'}$, $R^{5'}$, $R^{8'}$, $R^{9'}$, $R^{10'}$, $R^{11'}$, $R^{14'}$, and $R^{15'}$, any two or more of which may be the same or different, each represent a hydrogen atom or an alkyl group having 1 to 4 carbon atoms; and n is as defined for general formula (2).

In formulae (2) and (3), n is 8 to 14, preferably 10 to 12, more preferably 10, in the interests of absorbance, compatibility with resins, and transparency.

Examples of the triazine compound of formula (1) that can be used in the invention include Compound Nos. 1 to 4A shown below.

wherein $R^A$, $R^B$, $R^C$, and $R^D$, any two or more of which may be the same or different, each represent a hydrogen atom or an alkyl group having 1 to 4 carbon atoms.

[Chem. 3A]

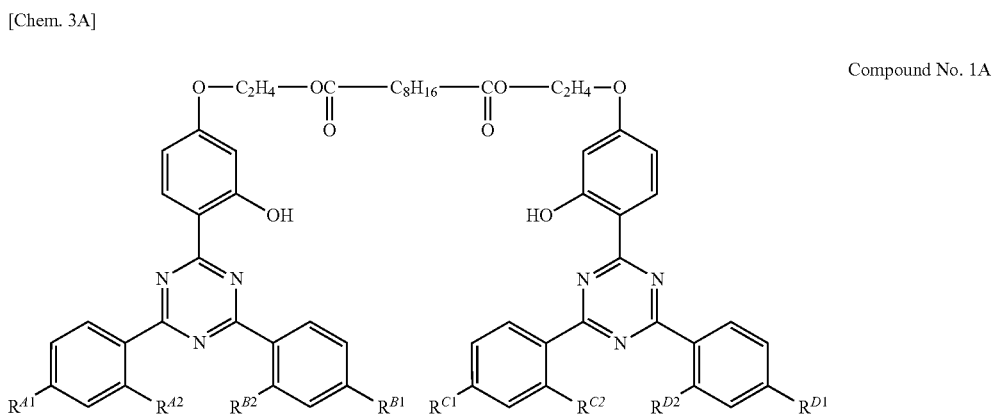

wherein $R^{A1}$, $R^{A2}$, $R^{B1}$, $R^{B2}$, $R^{C1}$, $R^{C2}$, $R^{D1}$ and $R^{D2}$, any two or more of which may be the same or different, each represent a hydrogen atom or an alkyl group having 1 to 4 carbon atoms.

[Chem. 4]

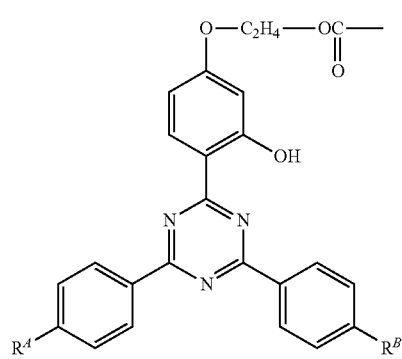

Compound No. 2

-continued

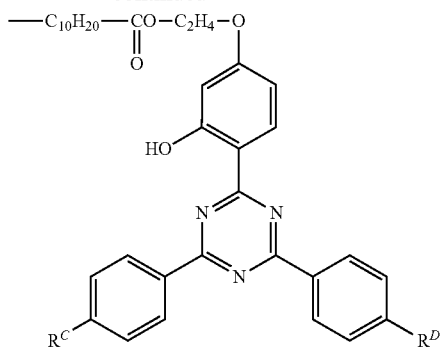

wherein $R^A$, $R^B$, $R^C$, and $R^D$, any two or more of which may be the same or different, each represent a hydrogen atom or an alkyl group having 1 to 4 carbon atoms.

[Chem. 4A]

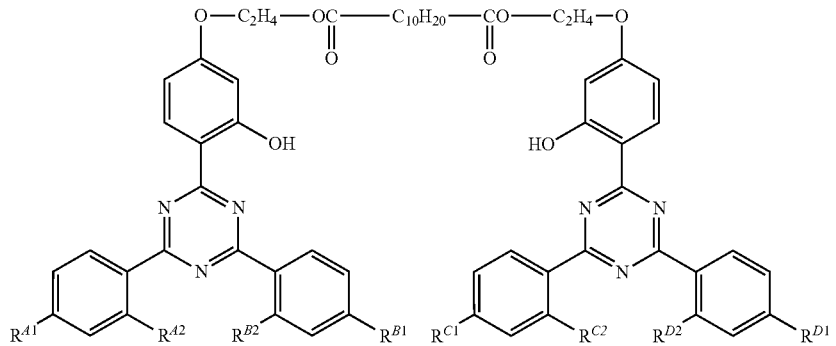

Compound No. 2A wherein $R^{A1}$, $R^{A2}$, $R^{B1}$, $R^{B2}$, $R^{C1}$, $R^{C2}$, $R^{D1}$ and $R^{D2}$, any two or more of which may be the same or different, each represent a hydrogen atom or an alkyl group having 1 to 4 carbon atoms.

[Chem. 5]

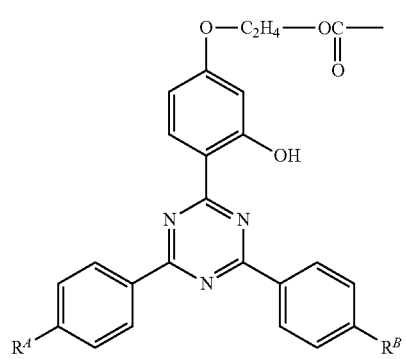

Compound No.3

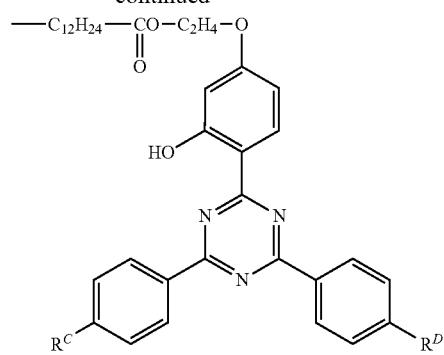

wherein $R^A$, $R^B$, $R^C$, and $R^D$, any two or more of which may be the same or different, each represent a hydrogen atom or an alkyl group having 1 to 4 carbon atoms.

[Chem. 5A]

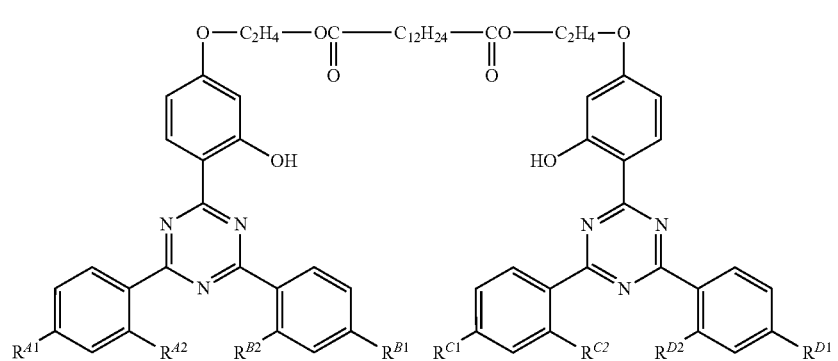

Compound No. 3A wherein $R^{A1}$, $R^{A2}$, $R^{B1}$, $R^{B2}$, $R^{C1}$, $R^{C2}$, $R^{D1}$ and $R^{D2}$, any two or more of which may be the same or different, each represent a hydrogen atom or an alkyl group having 1 to 4 carbon atoms.

[Chem. 6]

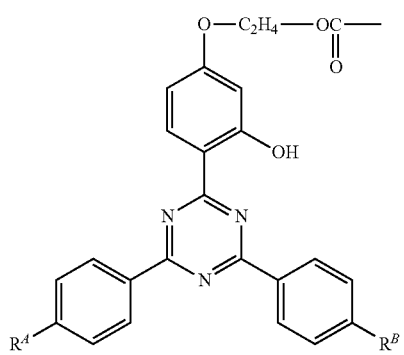

Compound No.4

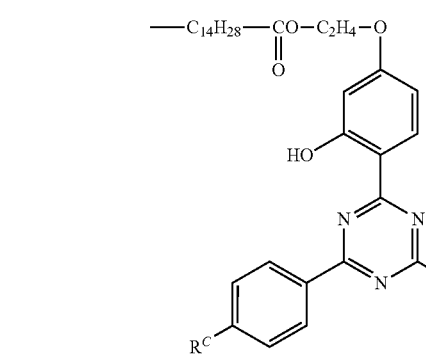

wherein $R^A$, $R^B$, $R^C$, and $R^D$, any two or more of which may be the same or different, each represent a hydrogen atom or an alkyl group having 1 to 4 carbon atoms.

[Chem. 7]

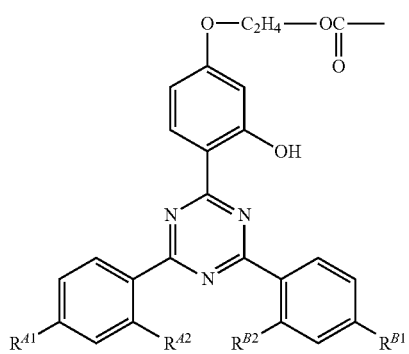

Compound No.4A

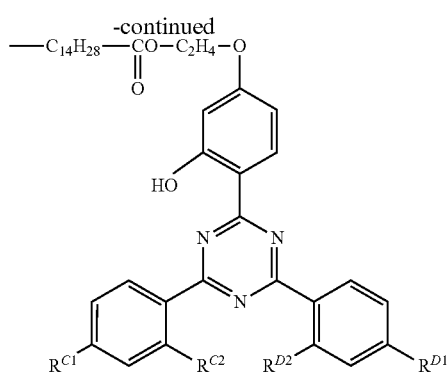

wherein $R^{A1}$, $R^{A2}$, $R^{B1}$, $R^{B2}$, $R^{C1}$, $R^{C2}$, $R^{D1}$ and $R^{D2}$, any two or more of which may be the same or different, each represent a hydrogen atom or an alkyl group having 1 to 4 carbon atoms.

The triazine compound of formula (1) can be prepared by any known process. For example, a Compound No. 1 wherein $R^A$, $R^B$, $R^C$, and $R^D$ are all hydrogen may be prepared by esterification or interesterification between 2-[2-hydroxy-4-(2-hydroxyethyloxy)phenyl]-4,6-diphenyl-1,3,5-triazine as an alcohol component and an ester-deriving compound of the corresponding dicarboxylic acid, such as a dicarboxylic acid, a dicarboxylic acid dihalide, or a dicarboxylic acid diester. In this case, sebacic acid is used as the corresponding dicarboxylic acid.

The triazine compound of formula (1) according to the invention is incorporated into a synthetic resin as a UV absorber to provide a synthetic resin composition useful for a variety of applications as will be noted later.

The synthetic resin composition of the invention will then be described.

The synthetic resin composition of the invention comprises a synthetic resin having incorporated therein the triazine compound of formula (1) of the invention as a UV absorber.

The content of the triazine compound in the synthetic resin composition of the invention is 0.001 to 20 parts by mass. The content is preferably 0.001 to 10 parts by mass, more preferably 0.003 to 8 parts by mass, even more preferably 0.005 to 5 parts by mass, in terms of compatibility with a resin, heat resistance, weatherability, and volatilization resistance. When the content is less than 0.001 parts, the composition has poor heat resistance and weatherability. When the content is more than 20 parts, the composition has poor compatibility with a resin.

Examples of the synthetic resin that can be used in the invention include thermoplastic resins and thermosetting resins. Examples of the thermoplastic resins include polyolefins and copolyolefins, such as polypropylene, high density polyethylene, low density polyethylene, linear low density polyethylene, poly-α-olefins (e.g., polybutene-1 and poly-4-methylpentene), ethylene-vinyl acetate copolymers, and ethylene-propylene copolymers; halogen-containing resins, such as polyvinyl chloride, polyvinylidene chloride, chlorinated rubber, vinyl chloride-vinyl acetate copolymers, vinyl chloride-ethylene copolymers, vinyl chloride-vinylidene chloride copolymers, vinyl chloride-vinylidene chloride-vinyl acetate terpolymers, vinyl chloride-acrylic ester copolymers, vinyl chloride-maleic ester copolymers, and vinyl chloride-cyclohexylmaleimide copolymers; petroleum resins; chromane resins; polystyrene; polyvinyl acetate; acrylic resins; copolymers of styrene and/or α-methylstyrene with another monomer (e.g., maleic anhydride, phenylmaleimide, methyl methacrylate, butadiene, or acrylonitrile), such as AS resins, ABS resins, MBS resins, and heat resistant ABS resins; linear polyesters, such as polymethyl methacrylate, polyvinyl alcohol, polyvinyl formal, polyvinyl butyral, polyethylene terephthalate, polybutyl terephthalate, and polytetramethyl terephthalate; polyphenylene oxide; polyamides, such as polycaprolactam and polyhexamethylene adipamide; thermoplastic resins, such as polycarbonates, branched polycarbonates, polyacetal, polyphenylene sulfide, polyurethane, and cellulosic resins; and mixtures of these thermoplastic resins. Examples of the thermosetting resins include phenol resins, urea resins, melamine resins, epoxy resins, and unsaturated polyester resins. Also included in useful synthetic resins are elastomers, such as isoprene rubber, butadiene rubber, acrylonitrile-butadiene copolymer rubber, and styrene-butadiene copolymer rubber. The above enumerated resins may contain such elastomers.

The above described synthetic resins may be used irrespective of molecular weight, degree of polymerization, density, softening point, solvent-insoluble content, degree of stereoregularity, presence or absence of catalyst residue, type and copolymerization ratio of monomers, type of catalyst for polymerization (e.g., Ziegler type or metallocene type), and the like.

Preferred of the synthetic resins are polycarbonate resins, polyester resins, acrylic resins, and ABS resins from the viewpoint of the compatibility of the UV absorber and transparency.

Any commercially supplied polycarbonate resins may be used, including those obtained by the reaction between at least one bisphenol and phosgene or a carbonic acid diester and those obtained by interesterification between at least one bisphenol and a diphenyl carbonate. Examples of the bisphenol include hydroquinone, 4,4-dihydroxyphenyl, bis(4-hydroxyphenyl)alkanes, bis(4-hydroxyphenyl)cycloalkanes, bis(4-hydroxyphenyl) sulfide, bis(4-hydroxyphenyl) ether, bis(4-hydroxyphenyl) ketone, bis(4-hydroxyphenyl) sulfone, bisphenol fluorene, and their alkyl-, aryl-, or halogen-substituted derivatives. These polycarbonate resins may be used either alone or in combination of two or more thereof. Of the polycarbonate resins, preferred is a bisphenol A polycarbonate resin prepared from 2,2-bis(4-hydroxyphenyl)propane (also called bisphenol A) because of its ready availability.

The polycarbonate resin may be used either alone or as blended with other resins to form a polymer alloy. Examples of such a polymer alloy include polycarbonate/ABS resin, polycarbonate/AS resin, polycarbonate/rubber polymer, polycarbonate/ABS resin/rubber polymer, polycarbonate/polyethylene terephthalate, polycarbonate/polybutylene terephthalate, polycarbonate/ASA resin, and polycarbonate/AES resin. The proportion of the resin other than the polycarbonate resin in the polymer alloy is preferably not more than 40 mass %.

In using a polycarbonate resin as a synthetic resin, the content of the triazine compound of formula (1) in the synthetic resin composition is 0.001 to 20 parts by mass per 100 parts by mass of the polycarbonate resin. The content is preferably 0.01 to 10 parts by mass, more preferably 0.1 to 5 parts by mass, in view of heat resistance, weatherability, and compatibility.

If desired, the synthetic resin composition of the invention may contain a phenol antioxidant, a phosphorus antioxidant, a thioether antioxidant, a hindered amine light stabilizer, a triazine ring-containing compound, a metal hydroxide, a phosphoric ester flame retardant, a condensed phosphoric ester flame retardant, a phosphate flame retardant, an inorganic phosphorus flame retardant, a (poly)phosphate flame retardant, a halogen flame retardant, a silicone flame retardant, antimony oxide, an inorganic flame retardant aid, an organic flame retardant aid, an antistatic agent, a lubricant, a nucleating agent, a plasticizer, a parting agent, a compatibilizers, foaming agent, a light absorbing dye, a pigment, a dye, a processing aid, a metal deactivator, inorganic particles, an antibacterial, an antifungal, an extender, a filler, and so forth as long as the effects of the invention are not impaired. A UV absorber other than the triazine compound of formula (1) may also be used as long as the effects of the invention are not impaired. The total content of these additives is preferably not more than 10 parts by mass per 100 parts by mass of the synthetic resin.

Examples of useful phenol antioxidants include 2,6-di-tert-butyl-p-cresol, 2,6-diphenyl-4-octadecyloxyphenol, distearyl(3,5-di-tert-butyl-4-hydroxybenzyl)phosphonate, 1,6-hexamethylene bis[(3,5-di-tert-butyl-4-hydroxyphenyl)propionic acid amide], 4,4'-thiobis(6-tert-butyl-m-cresol), 2,2'-methylenebis(4-methyl-6-tert-butylphenol), 2,2'-methylenebis(4-ethyl-6-tert-butylphenol), 4,4'-butylidenebis(6-tert-butyl-m-cresol), 2,2'-ethylidenebis(4,6-di-tert-butylphenol), 2,2'-ethylidenebis(4-sec-butyl-6-tert-butylphenol), 1,1,3-tris(2-methyl-4-hydroxy-5-tert-butylphenyl)butane, 1,3,5-tris(2,6-dimethyl-3-hydroxy-4-tert-butylbenzyl)isocyanurate, 1,3,5-tris(3,5-di-tert-butyl-4-hydroxybenzyl)isocyanurate, 1,3,5-tris(3,5-di-tert-butyl-4-hydroxybenzyl)-2,4,6-trimethylbenzene, 2-tert-butyl-4-methyl-6-(2-acryloyloxy-3-tert-butyl-5-methylbenzyl)phenol, stearyl (3,5-di-tert-butyl-4-hydroxyphenyl)propionate, tetrakis[3-(3,5-di-tert-butyl-4-hydroxyphenyl)propionic acid methyl]methane, thiodiethylene glycol bis[(3,5-di-tert-butyl-4-hydroxyphenyl)propionate], 1,6-hexamethylene bis[(3,5-di-tert-butyl-4-hydroxyphenyl)propionate], bis[3,3-bis(4-hydroxy-3-tert-butylphenyl)butyric acid] glycol ester, bis[2-tert-butyl-4-methyl-6-(2-hydroxy-3-tert-butyl-5-methylbenzyl)phenyl] terephthalate, 1,3,5-tris[(3,5-di-tert-butyl-4-hydroxyphenyl)propionyloxyethyl]isocyanurate, 3,9-bis[1,1-dimethyl-2-{(3-tert-butyl-4-hydroxy-5-methylphenyl)propionyloxy}ethyl]-2,4,8,10-tetraoxaspiro[5,5]undecane, and triethylene glycol bis[(3-tert-butyl-4-hydroxy-5-methylphenyl)propionate]. The amount of the phenol antioxidant, if added, is preferably 0.001 to 10 parts, more preferably 0.05 to 5 parts, by mass per 100 parts by mass of the synthetic resin.

Examples of useful phosphorus antioxidants include trisnonylphenyl phosphite, tris[2-tert-butyl-4-(3-tert-butyl-4-hydroxy-5-methylphenylthio)-5-methylphenyl]phosphite, tridecyl phosphite, octyldiphenyl phosphite, di(decyl)monophenyl phosphite, di(tridecyl)pentaerythritol diphosphite, di(nonylphenyl)pentaerythritol diphosphite, bis(2,4-di-tert-butylphenyl)pentaerythritol diphosphite, bis(2,6-di-tert-butyl-4-methylphenyl)pentaerythritol diphosphite, bis(2,4,6-tri-tert-butylphenyl)pentaerythritol diphosphite, bis(2,4-dicumylphenyl)pentaerythritol diphosphite, tetra(tridecyl)isopropylidenediphenol diphosphite, tetra(tridecyl)-4,4'-n-butylidenebis(2-tert-butyl-5-methylphenol) diphosphite, hexa(tridecyl)-1,1,3-tris(2-methyl-4-hydroxy-5-tert-butylphenyl)butane triphosphite, tetrakis(2,4-di-tert-butylphenyl) biphenylene diphosphonite, 9,10-dihydro-9-oxa-10-phosphaphenanthrene 10-oxide, 2,2'-methylenebis(4,6-tert-butylphenyl)-2-ethylhexyl phosphite, 2,2'-methylenebis(4,6-tert-butylphenyl)octadecyl phosphite, 2,2'-ethylidenebis(4,6-di-tert-butylphenyl) fluorophosphite, tris(2-[(2,4,8,10-tetrakis-tert-butyldibenzo[d,f][1,3,2]dioxaphosphepin-6-yl)

oxy]ethyl)amine, and phosphite of 2-ethyl-2-butylpropylene glycol and 2,4,6-tri-tert-butylphenol. The amount of the phosphorus antioxidant, if added, is preferably 0.001 to 10 parts, more preferably 0.05 to 5 parts, by mass 100 parts by mass of the synthetic resin.

Examples of useful thioether antioxidants include dialkyl thiodipropionates, such as dilauryl thiodipropionate, dimyristyl thiodipropionate, and distearyl thiodipropionate, and a pentaerythritol tetra(β-alkylthiopropionate). The amount of the thioether antioxidant, if added, is preferably 0.001 to 10 parts, more preferably 0.05 to 5 parts, by mass per 100 parts by mass of the synthetic resin.

Examples of useful hindered amine light stabilizers include hindered amine compounds, such as 2,2,6,6-tetramethyl-4-piperidyl stearate, 1,2,2,6,6-pentamethyl-4-piperidyl stearate, 2,2,6,6-tetramethyl-4-piperidyl benzoate, bis(2,2,6,6-tetramethyl-4-piperidyl) sebacate, bis(1,2,2,6,6-tetramethyl-4-piperidyl) sebacate, bis(1-oxtoxy-2,2,6,6-tetramethyl-4-piperidy) sebacate, tetrakis(2,2,6,6-tetramethyl-4-piperidyl)-1,2,3,4-butanetetracarboxylate, tetrakis(1,2,2,6,6-pentamethyl-4-piperidyl)-1,2,3,4-butanetetracarboxylate, bis(2,2,6,6-tetramethyl-4-piperidyl)di(tridecyl)-1,2,3,4-butanetetracarboxylate, bis(1,2,2,6,6-pentamethyl-4-piperidyl)di(tridecyl)-1,2,3,4-butanetetracarboxylate, bis(1,2,2,4,4-pentamethyl-4-piperidyl)-2-butyl-2-(3,5-di-tert-butyl-4-hydroxybenzyl) malonate, 1-(2-hydroxyethyl)-2,2,6,6-tetramethyl-4-piperidinol/diethyl succinate polycondensates, 1,6-bis(2,2,6,6-tetramethyl-4-piperidylamino)hexane/2,4-dichloro-6-morpholino-s-triazine polycondensates, 1,6-bis(2,2,6,6-tetramethyl-4-piperidylamino)hexane/2,4-dichloro-6-tert-octylamino-s-triazine polycondensates, 1,5,8,12-tetrakis[2,4-bis(N-butyl-N-(2,2,6,6-tetramethyl-4-piperidyl)amino)-s-triazin-6-yl]-1,5,8,12-tetraazadodecane, 1,5,8,12-tetrakis[2,4-bis(N-butyl-N-(1,2,2,6,6-pentamethyl-4-piperidyl)amino)-s-triazin-6-yl]-1,5,8,12-tetraazadodecane, 1,6,11-tris[2,4-bis(N-butyl-N-(2,2,6,6-tetramethyl-4-piperidyl)amino)-s-triazin-6-yl]aminoundecane, and 1,6,11-tris[2,4-bis(N-butyl-N-(1,2,2,6,6-pentamethyl-4-piperidyl)amino)-s-triazin-6-yl]aminoundecane. The amount of the hindered amine light stabilizer, if added, is preferably 0.001 to 30 parts, more preferably 0.05 to 10 parts, by mass per 100 parts by mass of the synthetic resin.

Examples of useful triazine ring-containing compounds are melamine, ammeline, benzoguanamine, acetoguanamine, phthalodiguanamine, melamine cyanurate, melamine pyrophosphate, butylene diguanamine, norbornene diguanamine, methylene diguanamine, ethylene dimelamine, trimethylene dimelamine, tetramethylene dimelamine, hexamethylene dimelamine, and 1,3-hexylene dimelamine.

Examples of useful metal hydroxides include magnesium hydroxide, aluminum hydroxide, calcium hydroxide, barium hydroxide, zinc hydroxide, and KISUMA 5A (trade name of magnesium hydroxide manufactured by Kyowa Chemical industry Co., Ltd.).

Examples of useful phosphoric ester flame retardants include trimethyl phosphate, triethyl phosphate, tributyl phosphate, tributoxyethyl phosphate, trichloroethyl phosphate, trisdichloropropyl phosphate, triphenyl phosphate, tricresyl phosphate, cresyl diphenyl phosphate, trixylenyl phosphate, octyl diphenyl phosphate, xylenyl diphenyl phosphate, trisisopropyl phenyl phosphate, 2-ethylhexyl diphenyl phosphate, t-butylphenyl diphenyl phosphate, bis(t-butylphenyl) phenyl phosphate, tris(t-butylphenyl) phosphate, isopropyl phenyl diphenyl phosphate, bis(isopropylphenyl) diphenyl phosphate, and tris(isopropylphenyl) phosphate.

Examples of useful condensed phosphoric ester flame retardants include 1, 3-phenylenebis(diphenyl phosphate), 1,3-phenylenebis(dixylenyl phosphate), and bisphenol A bis (diphenyl phosphate).

Examples of useful (poly)phosphate flame retardants include ammonium salts and amine salts of (poly)phosphoric acids, such as ammonium polyphosphate, melamine polyphosphate, piperazine polyphosphate, melamine pyrophosphate, and piperazine pyrophosphate.

Examples of useful inorganic flame retardant aids include inorganic compounds, such as titanium oxide, aluminum oxide, magnesium oxide, hydrotalcite, talc, and montmorillonite, and surface-treated products of these inorganic compounds.

Commercially available products of inorganic flame retardant aids may be used, including TIPAQUE R-680 (titanium oxide from Ishihara Sangyo Kaisha, Ltd.), KYOWAMAG 150 (magnesium oxide from Kyowa Chemical industry Co., Ltd.), DHT-4A (hydrotalcite from Kyowa Chemical industry Co., Ltd.), and Alcamizer 4 (zinc-modified hydrotalcite from Kyowa Chemical industry Co., Ltd.).

Examples of useful organic flame retardant aids include pentaerythritol.

Examples of useful antistatic agents include cationic antistatics, such as fatty acid quaternary ammonium ion salts and quaternary polyamine salts; anionic antistatics, such as higher alcohol phosphoric ester salts, higher alcohol EO adducts, polyethylene glycol fatty acid esters, anionic alkylsulfonates, higher alcohol sulfuric ester salts, higher alcohol ethylene oxide-added sulfuric ester salts, and higher alcohol ethylene oxide-added phosphoric ester salts; nonionic antistatics, such as polyhydric alcohol fatty acid esters, polyglycol phosphoric esters, and polyoxyethylene alkyl allyl ethers; and amphoteric antistatics, such as amphoteric alkyl betaines, e.g., alkyl dimethylaminoacetic acid betaine, and amphoteric imidazoline surfactants.

Examples of useful lubricants include hydrocarbon lubricants, such as liquid paraffin, paraffin wax, and polyethylene wax; aliphatic lubricants, such as stearyl alcohol, stearic acid, and 12-hydroxystearic acid; amide lubricants, such as stearamide, oleamide, erucamide, methylenebisstearamide, and ethylenestearamide; metal soap lubricants, such as calcium stearate, zinc stearate, magnesium stearate, lead stearate, aluminum stearate, barium stearate, a barium stearate/zinc stearate composite, and a zinc stearate/calcium stearate composite; and ester lubricants, such as hydrogenated fats and oils, glycerol monostearate, butyl stearate, pentaerythritol stearate, and stearyl stearate.

Examples of useful nucleating agents include dibenzylidene sorbitol, bis(p-methylbenzylidene) sorbitol, bis(p-ethylbenzylidene) sorbitol, aluminum hydroxy-di-(t-butyl benzoate), sodium bis(4-t-butylphenyl)phosphate, and sodium 2,2-methylenebis(4,6-di-t-butylphenyl)phosphate.

Examples of useful plasticizers include phthalic esters, dibasic acid esters, chlorinated paraffin, polyesters, epoxidized esters, phosphoric esters, and trimellitic esters.

Examples of useful extenders include calcium silicate powder, silica powder, talc powder, mica powder, alumina powder, titanium oxide powder, and glass flakes.

Examples of useful fillers include glass fiber, and carbon fiber.

Examples of useful UV absorbers other the triazine compound of formula (1) include 2-hydroxybenzophenones, such as 2,4-dihydroxybenzophenone, 2-hydroxy-4-methoxybenzophenone, 2-hydroxy-4-octoxybenzophenone, and 5,5'-methylenebis(2-hydroxy-4-methoxybenzophenone); 2-(2'-hydroxyphenyl)benzotriazoles, such as 2-(2'- hydroxy-5'-methylphenyl)benzotriazole, 2-(2'-hydroxy-3', 5'-di-tert-butylphenyl)-5-chlorobenzotriazole, 2-(2'-hydroxy-3'-tert-butyl-5'-methylphenyl)-5-chlorobenzotriazole, 2-(2'-hydroxy-5'-tert-octylphenyl) benzotriazole, 2-(2'-hydroxy-3',5'-dicumylphenyl) benzotriazole, 2,2'-methylenebis(4-tert-octyl-6-(benzotriazolyl)phenol), and 2-(2'-hydroxy-3'-tert-butyl-5'-carboxyphenyl)benzotriazole; benzoates, such as phenyl salicylate, resorcinol monobenzoate, 2,4-di-tert-butylphenyl-3,5-di-tert-butyl-4-hydroxybenzoate, 2,4-di-tert-amylphenyl-3,5-di-tert-butyl-4-hydroxybenzoate, and hexadecyl-3,5-di-tert-butyl-4-hydroxybenzoate; substituted oxanilides, such as 2-ethyl-2'-ethoxyoxanilide and 2-ethoxy-4'-dodecyloxanilide; cyanoacrylates, such as ethyl-α-cyano-β,β-diphenylacrylate, methyl-2-cyano-3-methyl-3-(p-methoxyphenyl)acrylate, and pentaerythritol tetrakis(2-cyano-3,3-diphenylacrylate); and triaryl triazines, such as 2-(2-hydroxy-4-octoxyphenyl)-4,6-bis(2,4-di-tert-butylphenyl)-s-triazine, 2-(2-hydroxy-4-methoxyphenyl)-4,6-diphenyl-s-triazine, and 2-(2-hydroxy-4-propoxy-5-methylphenyl)-4,6-bis(2,4-di-tert-butylphenyl)-s-triazine.

The amount of the other UV absorber, if used, is preferably not more than 5 parts by mass per 100 parts by mass of the synthetic resin.

The method for preparing the synthetic resin composition of the invention is not particularly limited, and any method known for making a resin composition can be used.

For example, a synthetic resin, the UV absorber of formula (1), and, if necessary, other additives are premixed using various mixing machines, such as a tumbler mixer and a Henschel mixer, and the resulting mixture is melt kneaded using a Banbury mixer, a roll mill, a Brabender plastograph mixer, a single screw kneading extruder, a twin screw kneading extruder, a kneader, and the like.

The components, part of which may be premixed, may individually be fed through respective feeders to an extruder, where they are melt kneaded to make a resin composition. Part of the components may be premixed, and the mixture is melt kneaded in an extruder to prepare a masterbatch, which can then be mixed with the rest of the components to prepare a resin composition.

The synthetic resin composition of the invention can be molded to make molded articles excellent in weatherability and transparency. The molding techniques include, but are not limited to, extrusion, calendering, injection molding, roll molding, compression molding, blown film extrusion, and rotational molding. The synthetic resin composition can be molded into molded articles of various shapes, such as plates, sheets, films, bottles, fibers, and irregular shapes.

The synthetic resin composition in which a polycarbonate resin is used as the synthetic resin is suitable to obtain transparent molded articles.

The synthetic resin composition of the invention and the molded articles obtained therefrom are useful in various applications described below. In particular, the synthetic resin composition using a polycarbonate resin as the synthetic resin is preferably used in applications requiring weatherability and applications requiring transparency.

The synthetic resin composition and its molded articles of the invention find wide applications in various industrial fields, including electric and electronics, communications, agriculture, forestry and fisheries, mining, construction, foods, fibers, clothing, remedy, coal, petroleum, rubber, leather, automobiles, precision equipment, lumber, building materials, civil engineering, furniture, printing, musical instruments, and so on. Specifically, the applications include stationery and OA equipment, such as printers, personal computers, word processors, keyboards, PDAs (personal digital assistants), telephone sets, copiers, fax machines, ECRs (electronic cash registers), calculators, electronic diaries, cards, holders, and writing tools; household electric appliances, such as laundry machines, refrigerators, vacuum cleaners, microwave ovens, lighting equipment, game machines, irons, and kotatsu; audio and visual equipment, such as TV sets, VTRs, camcorders, radio-cassette recorders, tape recorders, mini discs, CD players, speakers, and liquid crystal displays; electric and electronic components and communication equipment, such as connectors, relays, capacitors, switches, printed circuit boards, coil bobbins, semiconductor sealants, LED sealants, electric wires, cables, transformers, deflection yokes, distribution boards, and clocks, housings (frames, cases, covers, and enclosures) and parts of OA equipment; automotive interior and exterior materials; materials for gas (petrol) vehicles, hybrid vehicles, electrical vehicles, train cars, boats, ships, aircrafts, buildings, and houses, such as seats (stuffing and upholstery), belts, ceiling covering, convertible tops, arm rests, door trims, rear package trays, carpets, mats, sun visors, wheel covers, mattress covers, air bags, insulating materials, assist grips, assist straps, wire covering, electrical insulators, paints, coatings, overlays, flooring, inside corner moldings, carpet, wallpaper, wall covering, exterior covering, interior covering, roofing, decks, walls, pillars, floor plates, fences, frames and moldings, profiles for windows and doors, roof shingles, siding boards, terraces, balconies, soundproofing boards, heat insulating boards, and window boards; civil engineering materials; and housewares and sporting equipment, such as clothing, curtains, bed sheets, chip boards, fiber boards, carpets and rugs, doormats, sheets, buckets, hoses, containers, glasses, bags, cases, goggles, skis, rackets, tents, and musical instruments.

EXAMPLES

The invention will now be illustrated in greater detail by way of Synthesis Examples, Examples, and Comparative Examples, but it should be understood that the invention is not limited thereto. Unless otherwise noted, all the parts are by mass.

Synthesis Example 1—Synthesis of Compound No. 1-1

A 1000 ml five-necked flask was equipped with a stirrer, a nitrogen inlet, a thermometer, a fractionating column, and a ball stopper (for sampling). The top of the fractionating column was fitted with a condenser and a distilling receiver. In the flask were put 86 g (0.2 mol) of 2-[2-hydroxy-4-(2-hydroxyethyloxy)phenyl]-4,6-diphenyl-1,3,5-triazine as an alcohol component, 20 g (0.1 mol) of sebacic acid as a dicarboxylic acid component, 300 g of xylene as a solvent, and 0.2 g (1 mmol) of sodium p-toluenesulfonate monohydrate as an esterification catalyst and heated at 130° C. under atmospheric pressure to conduct esterification reaction while driving produced water out of the system. The esterification reaction was ceased when the starting materials reduced to less than 1% as analyzed by HPLC. The reaction mixture was worked up by cooling for crystallization, followed by filtration to give Compound No. 1-1. Compound No. 1-1 is a Compound No. 1 in which $R^A$, $R^B$, $R^C$, and $R^D$ are all hydrogen atom. The product was identified to be Compound No. 1-1 using a high performance liquid chromatograph available from JASCO Corp. under conditions of a solvent of acetonitrile/water=95/5 (by volume), a flow rate of 1 ml/min, and a UV detection wavelength of 254 nm. The results of HPLC identification are as follows. The retention time of the desired product was 24.2 min.

Synthesis Example 2—Synthesis of Compound No. 2-1

An esterification reaction and working-up of the product were carried out in the same manner using the same reaction equipment as used in Synthesis Example 1, except for replacing the dicarboxylic acid component as one of the starting materials with 23 g (0.1 mol) of dodecanedioic acid, to prepare Compound No. 2-1, which is a Compound No. 2 in which $R^A$, $R^B$, $R^C$, and $R^D$ are all hydrogen atom. Identification of the product was carried out in the same manner as in Synthesis Example 1. The retention time of the desired product was 30.4 min.

Synthesis Example 3—Synthesis of Compound No. 2A-1

An esterification reaction and working-up of the product were carried out in the same manner using the same reaction equipment as used in Synthesis Example 1, except for replacing the alcohol component as one of the starting materials with 88 g (0.2 mol) of 2-[2-hydroxy-4-(2-hydroxyethyloxy)phenyl]-4,6-bis(2,4-dimethylphenyl)-1,3,5-triazine, to prepare Compound No. 2A-1, which is a Compound No. 2A in which $R^{A1}$, $R^{A2}$, $R^{B1}$, $R^{B2}$, $R^{C1}$, $R^{C2}$, $R^{D1}$, and $R^{D2}$ are all methyl group. Identification of the product was carried out in the same manner as in Synthesis Example 1. The retention time of the desired product was 27.6 min.

Synthesis Example 4—Synthesis of Compound No. 3-1

An esterification reaction and working-up of the product were carried out in the same manner using the same reaction equipment as used in Synthesis Example 1, except for replacing the dicarboxylic acid component as one of the starting materials with 26 g (0.1 mol) of is tetradecanedioic acid, to prepare Compound No. 3-1, which is a Compound No. 3 in which $R^A$, $R^B$, $R^C$, and $R^D$ are all hydrogen atom. Identification of the product was carried out in the same manner as in Synthesis Example 1. The retention time of the desired product was 36.5 min.

Synthesis Example 5—Synthesis of Compound No. 4-1

An esterification reaction and working-up of the product were carried out in the same manner using the same reaction equipment as used in Synthesis Example 1, except for replacing the dicarboxylic acid component as one of the starting materials with 29 g (0.1 mol) of is hexadecanedioic acid, to prepare Compound No. 4-1, which is a Compound No. 4 in which $R^A$, $R^B$, $R^C$, and $R^D$ are all hydrogen atom. Identification of the product was carried out in the same manner as in Synthesis Example 1. The retention time of the desired product was 40.2 min.

Examples 1-1 to 1-5 and Comparative Examples 1-1 to 1-3

The triazine compounds synthesized in Synthesis Examples 1 to 5 and Comparative Compounds 1 to 3 shown below were analyzed in a chloroform solvent at a concentration of 10 mg/l to determine maximum absorption wavelength ($\lambda_{max}$), absorbance ($A\lambda_{max}$), and molar extinction coefficient ($\varepsilon\lambda_{max}$) using a spectrophotometer V-670 (from JASCO Corp.). The results obtained are shown in Table 1 below.

TABLE 1

| | | Results of Evaluation | | |
|---|---|---|---|---|
| | Compound No. | $\lambda_{max}$ | $A_{\lambda max}$ | $\varepsilon_{\lambda max}$ |
| Example 1-1 | 1-1 | 278 | 0.91 | $8.52 \times 10^4$ |
| Example 1-2 | 2-1 | 278 | 0.95 | $8.65 \times 10^4$ |
| Example 1-3 | 2A-1 | 290 | 0.84 | $7.66 \times 10^4$ |
| Example 1-4 | 3-1 | 278 | 0.88 | $8.57 \times 10^4$ |
| Example 1-5 | 4-1 | 278 | 0.80 | $7.75 \times 10^4$ |
| Compara. Example 1-1 | Compara. Compound 1 | 277 | 0.95 | $8.60 \times 10^4$ |
| Compara. Example 1-2 | Compara. Compound 2 | 278 | 0.85 | $4.00 \times 10^4$ |
| Compara. Example 1-3 | Compara. Compound 3 | 280 | 0.89 | $8.43 \times 10^4$ |

[Chem. 7]

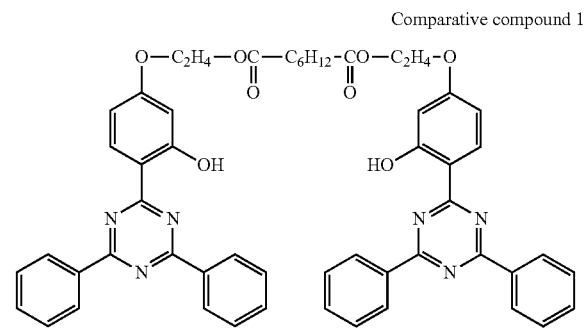

Comparative compound 1

[Chem. 8]

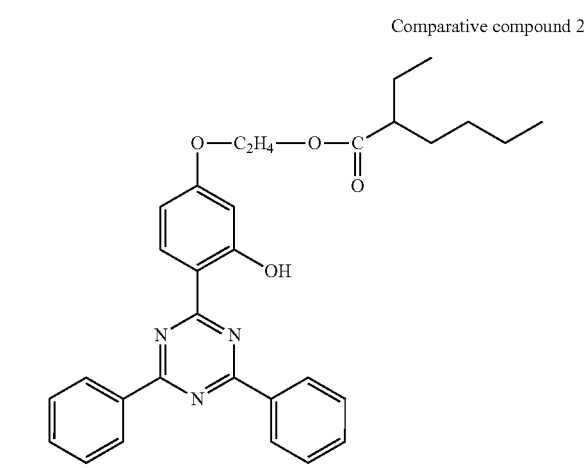

Comparative compound 2

[Chem. 9]

Comparative compound 3

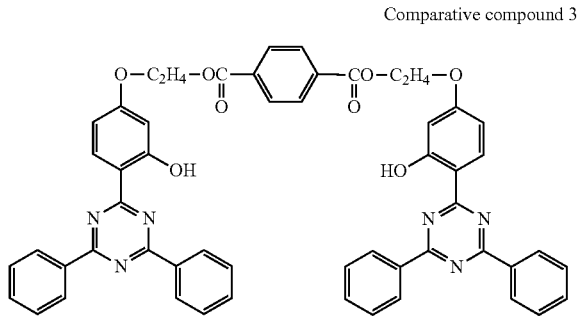

Examples 2-1 to 2-5 and Comparative Examples 2-1 to 2-3

One part of each of the triazine compounds synthesized in Synthesis Examples 1 to 5 and Comparative compounds 1 to 3 was put in a test tube and heated in air at 300° C. in a block bath for 15 minutes. After allowing to cool at room temperature for 1 hour, the degree of discoloration of the test compound was observed with the naked eye and rated on a scale below.

Visual Evaluation of Resistance to Discoloration (a 1 to 5 Scale):

Rating 1=good (pale yellow), Rating 2=fair (yellowish brown), Rating 3=medium (brown), Rating 4=poor (blackish brown), or Rating 5=bad (black). The results are shown in Table 2. Ratings 1 and 2 are good in coloration resistance, with the others rejected.

TABLE 2

|  | Compound No. | Evaluation Results Coloration Resistance |
|---|---|---|
| Example 2-1 | 1-1 | 2 |
| Example 2-2 | 2-1 | 2 |
| Example 2-3 | 2A-1 | 4 |
| Example 2-4 | 3-1 | 2 |
| Example 2-5 | 4-1 | 2 |
| Compara. Example 2-1 | Compara. Compound 1 | 2 |
| Compara. Example 2-2 | Compara. Compound 2 | 2 |
| Compara. Example 2-3 | Compara. Compound 3 | 2 |

Examples 3-1 to 3-5 and Comparative Examples 3-1 to 3-3

Evaluation for Resistance to Volatilization:

Each of the triazine compounds synthesized in Synthesis Examples 1 to 5 and Comparative Examples 1 to 3 was examined in terms of volatilization resistance by differential thermal analysis. The volatilization resistance was evaluated by the weight loss (%) on heating at 330° C. for 1 hour. The results are shown in Table 3.

TABLE 3

|  | Compound No. | Evaluation Results Weight Loss (%) |
|---|---|---|
| Example 3-1 | 1-1 | 16.3 |
| Example 3-2 | 2-1 | 12.1 |
| Example 3-3 | 2A-1 | 13.5 |
| Example 3-4 | 3-1 | 10.8 |
| Example 3-5 | 4-1 | 9.6 |
| Compara. Example 3-1 | Compara. Compound 1 | 20.8 |
| Compara. Example 3-2 | Compara. Compound 2 | 37.5 |
| Compara. Example 3-3 | Compara. Compound 3 | 18.8 |

Examples 4-1 to 4-5 and Comparative Examples 4-1 to 4-3

Preparation of Specimens:

A hundred parts of the synthetic resin shown in Table 4 was blended with each of the triazine compounds synthesized in Synthesis Examples 1 to 5 and Comparative Examples 1 to 3 of the amount shown in Table 4, and the blend was kneaded in an extruder (Labo-plastomill, from Toyo Seiki Seisakusho, Ltd.) and pelletized. The resulting pellets were injection molded at 280° C. to make 1 mm thick specimens for making the following evaluations. The results obtained are shown in Table 5.

TABLE 4

| Polycarbonate (Iupilon S-3000F, from Mitsubishi Engineering-Plastics Corp.) | 100 parts |
|---|---|
| Compound of Table 5 | 0.5 parts |

Haze (White Turbidity):
Haze was determined in accordance with JIS K7105.

Volatilization Resistance:
Volatilization resistance of the specimen containing each of the triazine compounds synthesized in Synthesis Examples 1 to 5 and Comparative Examples 1 to 3 was evaluated by the weight loss (%) on heating at 300° C. for 1 hour.

Resistance to Thermal Discoloration (Resistance to Initial Discoloration):
The yellowness index of the specimen immediately after the processing was measured by the transmission method using a multi-light source spectrocolorimeter from Suga Test Instruments Co., Ltd.

Bleed Resistance:
Bleed resistance of the specimen was observed after 30 days of storage at 60° C.

TABLE 5

|  |  | Results of Evaluation | | | |
|---|---|---|---|---|---|
|  | Compound No. | Haze | Volatilization Resistance | Thermal Discoloration Resistance | Bleed Resistance |
| Example 4-1 | 1-1 | 2 | 0.24 | 2 | good |
| Example 4-2 | 2-1 | 1.54 | 0.18 | 2 | excellent |
| Example 4-3 | 2A-1 | 1.68 | 0.20 | 4 | good |
| Example 4-4 | 3-1 | 1.58 | 0.16 | 2 | good |
| Example 4-5 | 4-1 | 1.50 | 0.14 | 2 | good |
| Compara. Example 4-1 | Compara. Compound 1 | 6.34 | 0.31 | 2 | no good |

TABLE 5-continued

| | Compound No. | Results of Evaluation | | | |
|---|---|---|---|---|---|
| | | Haze | Volatilization Resistance | Thermal Discoloration Resistance | Bleed Resistance |
| Compara. Example 4-2 | Compara. Compound 2 | 1.52 | 0.56 | 2 | good |
| Compara. Example 4-3 | Compara. Compound 3 | 5.26 | 0.28 | 2 | no good |

Examples 5-1 to 5-3

A 50 μm-thick polycarbonate cast film was prepared using the triazine compound shown in Table 6 in accordance with Film Casting Method 1 described below. The transparency of the resulting film was evaluated by haze determined by the transparency test method below. The appearance (while turbidity) of the film was evaluated by the method described below. The results of evaluations are shown in Table 6.

Film Casting Method 1:

A hundred grams of a commercially available polycarbonate resin (Iupilon S-3000F, from Mitsubishi Engineering-Plastics Corp.) and 1.0 g (1 phr) of a UV absorber were processed in an extruder (Labo-plastomill μ, from Toyo Seiki) at 280° C. and 50 rpm. In a 25 ml measuring flask was put 1.25 g of the resulting pellets, and dichloromethane was added to the mark. The system was allowed to stand at room temperature for about 1 hour to make a solution. Using a volumetric pipette, 4 ml of the solution was placed in a Petri dish (diameter: 60 mm) and allowed to dry at room temperature for 30 minutes. The dry film thus formed was peeled off the Petri dish to give a 50 μm thick polycarbonate cast film.

Transparency Test Method:

The haze of the resulting cast film was determined using a haze meter (Haze Guard II, from Toyo Seiki Seisakusho, Ltd.). A measurement was taken at five points of the film, and an average haze was calculated.

Evaluation of Appearance (White Turbidity):

The appearance of the cast film was observed with the naked eye and rated on an A to C scale: A=no turbidity; B=slightly turbid; C=turbid.

Comparative Example 5-1

A 50 μm thick polycarbonate cast film was made by Film Casting Method 1, except for using no UV absorber. The transparency of the resulting cast film in terms of haze was evaluated by the transparency test method described supra. The white turbidity of the film was visually observed and rated in the same manner as described supra. The results obtained are shown in Table 6.

Comparative Example 5-2

A 50 μm thick polycarbonate cast film was made by Film Casting Method 1, except for using Comparative Compound 1. The transparency of the resulting cast film in terms of haze was evaluated by the transparency test method described above. The white turbidity of the film was visually observed and rated in the same manner as described above. The results obtained are shown in Table 6.

TABLE 6

| | Compound No. | Results of Evaluation | |
|---|---|---|---|
| | | Appearance (white turbidity) | Transparency (Haze) (%) |
| Example 5-1 | 2-1 | A | 1.45 |
| Example 5-2 | 1-1 | B | 2.88 |
| Example 5-3 | 3-1 | A | 1.48 |
| Comp. Example 5-1 | — | A | 1.09 |
| Comp. Example 5-2 | Compara. Compound 1 | C | 5.12 |

Example 6

A polycarbonate cast film was prepared using Compound No. 2-1 as a triazine compound in accordance with Film Casting Method 2 below. The weatherability of the resulting film was evaluated by the weatherability test method below. The heat resistance of Compound No. 2-1 used in the cast film was evaluated by the heat resistance test method described below. The results of evaluations are shown in Table 7.

Film Casting Method 2:

A hundred grams of a commercially available polycarbonate resin (Iupilon S-3000F, from Mitsubishi Engineering-Plastics Corp.) and 2.0 g (2 phr) or 5.0 g (5 phr) of a UV absorber were processed in an extruder (Labo-plastomill μ, from Toyo Seiki) at 280° C. and 50 rpm. In a 25 ml measuring flask was put 1.25 g of the resulting pellets, and dichloromethane was added to the mark. The system was allowed to stand at room temperature for about 1 hour to make a solution. Using a volumetric pipette, 4 ml of the solution was placed in a Petri dish (diameter: 60 mm) and allowed to dry at room temperature for 30 minutes. The dry film thus formed was peeled off the Petri dish to give a 50 μm thick polycarbonate cast film.

Weatherability Test Method:

The cast film obtained by Film Casting Method 2 was subjected to an accelerated weathering test using Atlas Weather Ometer ci4000 at 65° C. with a water spray for 6000 hours. The transparency (haze) of the film was determined before and after the test. Further, the yellowness index, as an indication of discoloration resistance, of the film was determined by the method below before and after the test.

Test Method for Yellowness Index:

The yellowness index (YI) of the cast film was determined by the transmission method using a multi-light source spectrocolorimeter from Suga Test Instruments Co., Ltd.

Heat Resistance Test Method:

Each UV absorber was analyzed on a TGA/TDA Thermo plus EVO, from Rigaku Corp. The weight losses (mass %) were determined when the sample was heated in a 200 ml/min air stream from 30° C. up to 400° C. at a heating rate of 10° C./min and in a 200 ml/min air stream at a heating rate of 10° C./min from 30° C. up to 300° C., at which the sample was maintained for 30 minutes and 60 minutes.

Comparative Examples 6-1 and 6-2

A polycarbonate cast film was prepared by Film Casting Method 2 using 2.0 g of Comparative Compound 2 shown above or Comparative Compound 4 shown below.

A weatherability test was carried out on the resulting polycarbonate cast film by the above described weatherability test method. The heat resistance of Comparative Compound 2 used in the cast film was evaluated by the above described heat resistance test method. The results obtained are shown in Table 7.

[Chem.10]

Comparative compound 4

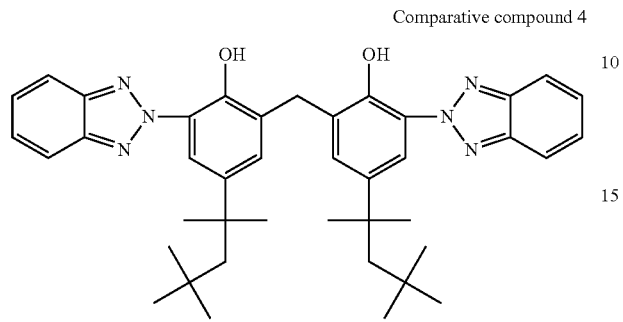

TABLE 7

| | | Compara. Example 6 | Compara. Example 6-1 | Compara. Example 6-2 |
|---|---|---|---|---|
| Compound No. | | 2-1 | Compara. Compound 1 | Compara. Compound 4 |
| Heat Resistance Test (mass %) | 300° C. × 30 mins | 2.0 | 13.2 | 10.1 |
| | 300° C. × 60 minutes | 5.5 | 24.8 | 19.0 |
| | up 400° C. | 9.0 | 32.4 | 34.8 |
| Weatherability Test (Haze) (%) | 0 hr | 1.53 | 2.50 | 2.38 |
| | 6000 hrs | 6.04 | 8.66 | 8.36 |
| | ΔHaze | 4.51 | 6.16 | 5.98 |
| Weatherability Test (YI) | 0 hr | 1.43 | 1.91 | 1.52 |
| | 6000 hrs | 2.55 | 4.65 | 4.81 |
| | ΔYI | 1.12 | 2.74 | 3.29 |

The invention claimed is:

1. A triazine compound represented by formula (1):

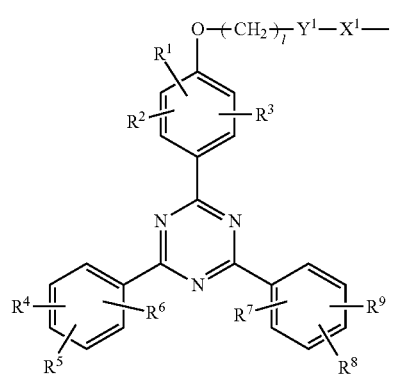

(1)

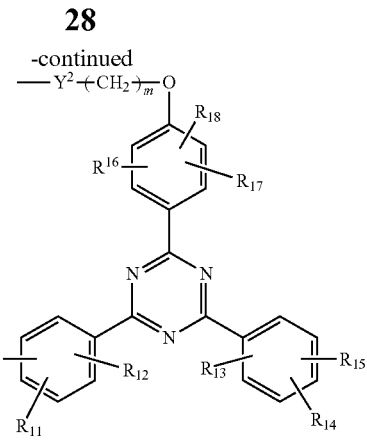

wherein $X^1$ represents a straight-chain alkylene group represented by —$(CH_2)_n$—, wherein n represents an integer of 8 to 14; $Y^1$ represents —OCO— and $Y^2$ represents —COO—; $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ any two or more of which may be the same or different, each represent a hydrogen atom, a hydroxy group, a halogen atom, an alkyl group having 1 to 20 carbon atoms, a alkenyl group having 3 to 20 carbon atoms, an alkoxy group having 1 to 20 carbon atoms, or an aryl group having 6 to 20 carbon atoms; and l and m, which may be the same or different, each represent an integer of 2 to 8.

2. The triazine compound according to claim 1, being represented by formula (2):

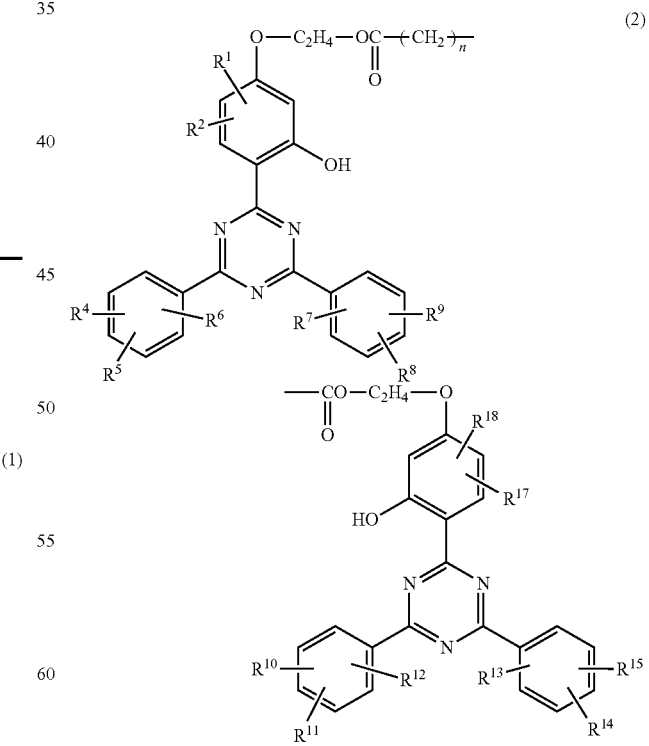

(2)

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{17}$, $R^{18}$, and n are as defined for an formula (1).

3. The triazine compound according to claim 1, being represented by formula (3):

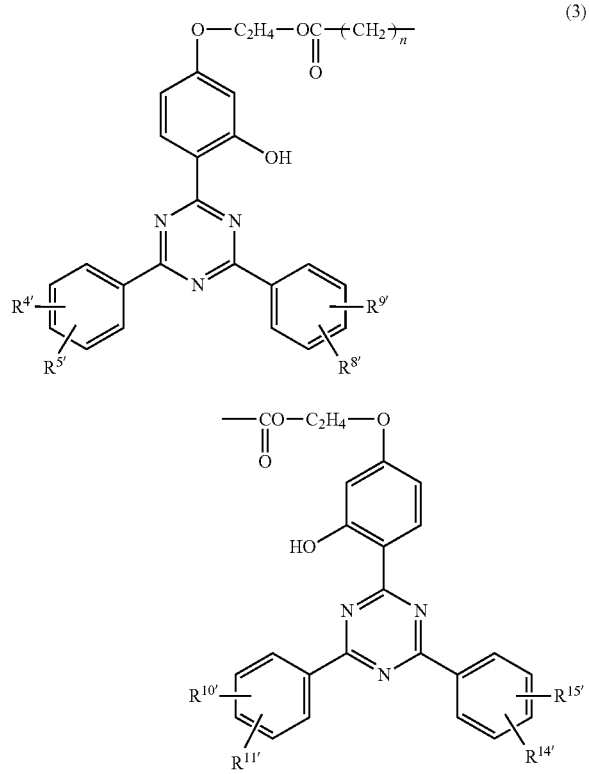

(3)

wherein $R^{4'}$, $R^{5'}$, $R^{8'}$, $R^{9'}$, $R^{10'}$, $R^{11'}$, $R^{14'}$, and $R^{15'}$, any two or more of which may be the same or different, each represent a hydrogen atom or an alkyl group having 1 to 4 carbon atoms; and n is as defined for formula (1).

4. A synthetic resin composition comprising 100 parts by mass of a synthetic resin and 0.001 to 20 parts by mass of the triazine compound according to claim 1.

5. The synthetic resin composition according to claim 4, wherein the synthetic resin is a polycarbonate resin, a polyester resin, an acrylic resin, or an ABS resin.

6. A molded article obtained from the synthetic resin composition according to claim 4.

7. A synthetic resin composition comprising 100 parts by mass of a synthetic resin and 0.001 to 20 parts by mass of the triazine compound according to claim 2.

8. A synthetic resin composition comprising 100 parts by mass of a synthetic resin and 0.001 to 20 parts by mass of the triazine compound according to claim 3.

9. A molded article obtained from the synthetic resin composition according to claim 5.

10. A molded article obtained from the synthetic resin composition according to claim 7.

11. A molded article obtained from the synthetic resin composition according to claim 8.

* * * * *